US008329192B2

(12) United States Patent
Straub et al.

(10) Patent No.: US 8,329,192 B2
(45) Date of Patent: *Dec. 11, 2012

(54) CAMPYLOBACTER POLYPEPTIDES AND METHODS OF USE

(75) Inventors: Darren E. Straub, New London, MN (US); Daryll A. Emery, New London, MN (US)

(73) Assignee: Epitopix LLC, Willmar, MN (US)

( * ) Notice: Subject to any disclaimer, the term of this patent is extended or adjusted under 35 U.S.C. 154(b) by 1350 days.

This patent is subject to a terminal disclaimer.

(21) Appl. No.: 10/945,847

(22) Filed: Sep. 20, 2004

(65) Prior Publication Data

US 2005/0095682 A1     May 5, 2005

Related U.S. Application Data

(60) Provisional application No. 60/504,119, filed on Sep. 19, 2003.

(51) Int. Cl.
A61K 39/02 (2006.01)
A61K 39/00 (2006.01)
A61K 38/00 (2006.01)

(52) U.S. Cl. ............... 424/234.1; 424/184.1; 424/816; 514/1.1

(58) Field of Classification Search ............ 424/234.1, 424/242.1, 9.2, 184.1, 242.2; 514/2
See application file for complete search history.

(56) References Cited

U.S. PATENT DOCUMENTS

| | | | |
|---|---|---|---|
| 4,003,792 A | 1/1977 | Mill et al. | 530/303 |
| 4,167,560 A | 9/1979 | Wohler, Jr. | 424/92 |
| 4,452,775 A | 6/1984 | Kent | 424/425 |
| 4,626,416 A | 12/1986 | DeVoe et al. | 423/12 |
| 4,663,161 A | 5/1987 | Mannino et al. | 424/450 |
| 4,681,761 A | 7/1987 | Mietzner et al. | 424/92 |
| 4,748,018 A | 5/1988 | Stolle et al. | 424/157.1 |
| 4,871,488 A | 10/1989 | Mannino et al. | 264/4.6 |
| 4,981,685 A | 1/1991 | Healey | 424/92 |
| 5,141,743 A | 8/1992 | Schryvers | 424/234.1 |
| 5,292,869 A | 3/1994 | Schryvers | 530/413 |
| 5,439,808 A | 8/1995 | Blake et al. | 435/69.1 |
| 5,534,256 A | 7/1996 | Potter et al. | 424/184.1 |
| 5,538,733 A | 7/1996 | Emery et al. | 424/422 |
| 5,578,314 A | 11/1996 | Cochrum et al. | 424/424 |
| 5,587,166 A | 12/1996 | Donachie | 424/422 |
| 5,688,682 A | 11/1997 | Mulks et al. | 435/252.1 |
| 5,830,479 A | 11/1998 | Emery et al. | 424/255.1 |
| 5,869,066 A | 2/1999 | Pace et al. | 424/282.1 |
| 5,885,589 A | 3/1999 | Foged et al. | 424/255.1 |
| 5,906,826 A | 5/1999 | Emery et al. | 424/422 |
| 6,027,736 A | 2/2000 | Emery et al. | 424/257.1 |
| 6,432,412 B1 | 8/2002 | Emery et al. | 424/241.1 |
| 6,682,754 B2 | 1/2004 | Emery et al. | 424/426 |
| 6,692,739 B1 | 2/2004 | Patti et al. | |
| 6,720,160 B2 | 4/2004 | Wolde-Mariam | 435/7.32 |
| 6,790,446 B2* | 9/2004 | Jacobs et al. | 424/184.1 |
| 7,138,124 B2 | 11/2006 | Emery et al. | 424/234.1 |
| 7,138,125 B2 | 11/2006 | Emery et al. | 424/234.1 |
| 7,147,857 B2 | 12/2006 | Emery et al. | 424/184.1 |
| 7,160,549 B2 | 1/2007 | Emery et al. | 435/69.3 |
| 7,341,732 B2 | 3/2008 | Emery et al. | |
| 7,371,393 B2* | 5/2008 | Emery et al. | 424/234.1 |
| 7,413,743 B2 | 8/2008 | Emery et al. | |
| 2003/0036639 A1 | 2/2003 | Emery et al. | |
| 2003/0064073 A1 | 4/2003 | Emery et al. | |
| 2003/0206922 A1 | 11/2003 | Emery et al. | |
| 2003/0211118 A1 | 11/2003 | Emery et al. | |
| 2004/0197350 A1 | 10/2004 | Emery et al. | |
| 2004/0197869 A1 | 10/2004 | Emery et al. | |
| 2004/0265329 A1 | 12/2004 | Emery et al. | |
| 2005/0186217 A1 | 8/2005 | Emery et al. | |
| 2006/0024323 A1 | 2/2006 | Emery et al. | |
| 2006/0165718 A1 | 7/2006 | Emery et al. | |
| 2007/0098733 A1 | 5/2007 | Emery et al. | |
| 2008/0293080 A1 | 11/2008 | Emery et al. | |
| 2009/0081236 A1 | 3/2009 | Emery et al. | |
| 2009/0123500 A1 | 5/2009 | Emery et al. | |
| 2009/0162402 A1 | 6/2009 | Emery et al. | |

FOREIGN PATENT DOCUMENTS

| | | |
|---|---|---|
| CA | 2029906 | 9/1990 |
| EP | 0 287 206 A1 | 10/1988 |
| EP | 0 287 206 B1 | 8/1993 |
| EP | 0 287 206 B2 | 8/1993 |
| WO | WO 90/11349 A1 | 10/1990 |
| WO | WO 90/12591 A1 | 11/1990 |
| WO | WO 95/21627 A1 | 8/1995 |
| WO | WO 96/01620 A1 | 1/1996 |
| WO | WO 01/37810 A2 | 5/2001 |
| WO | WO 01/37810 A3 | 5/2001 |

OTHER PUBLICATIONS

Widders et al. Vet. Microbiol. 64: 39-50, 1998.*
Zoete et al. Vaccine 25: 5548-5557, 2007.*
Rice et al. Vaccine 15: 1922-1932, 1997.*
Rinella et al. FEMS Microbiol. Lett. 262: 236-243, 2006.*
Abimiku et al. Epidem. Inf. 102: 271-280, 1989.*
Glisson et al. Avian Dis. 37: 1074-1079, 1993, abstract.*
Miyaji et al. Infect. Immun. 70: 5086-5090, 2002.*
Allos, "Association between *Campylobacter* Infection and Guillain-Barré Syndrome," *J. Infect. Dis.*, Dec. 1997;176(Suppl 2):S125-128.
Alurkar et al., "Immunomodulatory Properties of Porins of Some Members of the family *Enterobacteriaceae*," *Infection and Immunity*, Jun. 1997; 65(6):2382-2388.
Baig et al., "Utilization of Exogenous Siderophores by *Campylobacter* Species," *J. Clin. Microbiol.*, Mar. 1986;23(3):431-433.
Black et al., "Experimental *Campylobacter jejuni* Infection in Humans," *J. Infect. Dis.*, Mar. 1988;157(3):472-479.

(Continued)

Primary Examiner — S. Devi
(74) Attorney, Agent, or Firm — Mueting, Raasch & Gebhardt, P.A.

(57) ABSTRACT

The present invention provides isolated metal regulated polypeptides obtainable from a *Campylobacter* spp., and compositions including the polypeptides. The present invention also includes methods for using the compositions disclosed herein, including methods for treating in infection in a subject, for treating a condition caused by a *Campylobacter* spp., and for decreasing colonization of an animal.

6 Claims, 2 Drawing Sheets

OTHER PUBLICATIONS

Bock et al., "Whole-proteome interaction mining," *Bioinformatics*, Jan. 2003;19(1):125-134.

Caldwell et al., "Reversible Expression of Flagella in *Campylobacter jejuni*," *Infect. Immun.*, Dec. 1985;50(3):941-943.

Colles et al., "Genetic Diversity of *Campylobacter jejuni* Isolates from Farm Animals and the Farm Environment," *Appl. Environ. Microbiol.*, Dec. 2003;69(12):7409-7413.

Crosa, "Genetics and Molecular Biology of Siderophore-Mediated Iron Transport in Bacteria," *Microbiol. Rev.*, Dec. 1989; 53(4):517-530.

Dannenberg et al., "Melioidosis: Pathogenesis and Immunity in Mice and Hamsters. II. Studies With Avirulent Strains of Malleomyces Pseudomallei," *Am. J. Pathol.*, Nov.-Dec. 1958;34(6):1099-1121.

Dorrell et al., "Whole Genome Comparison of *Campylobacter jejuni* Human Isolates Using a Low-Cost Microarray Reveals Extensive Genetic Diversity," *Genome Res.*, Oct. 2001;11(10):1706-1715.

Field et al., "Influence of Iron on Growth, Morphology, Outer Membrane Protein Composition, and Synthesis of Siderophores in *Campylobacter jejuni*," *Infect. Immun.*, Oct. 1986;54(1):126-132.

Fox et al., "*Campylobacter jejuni* Infection in the ferret: An animal model of human campylobacteriosis," *Am. J. Vet. Res.*, Jan. 1987;48(1):85-90.

Galindo et al., "Cloning and Characterization of a *Campylobacter jejuni* Iron-Uptake Operon," *Curr. Microbiol.*, Feb. 2001;42(2):139-143.

Gilleland, Jr. et al., "Perspectives on the potential for successful development of outer membrane protein vaccines," *Eur J Clin Microbiol*. Jun. 1987;6(3):231-233. Review. (No abstract available.).

Guerry et al., "A Genetic Locus Involved in Iron Utilization Unique to Some *Campylobacter* Strains," *J. Bacteriol.*, Jun. 1997;179(12):3997-4002.

Harlow et al., "Antibodies, A Laboratory Manual," generally and Chapter 5, Cold Spring Harbor Laboratory, Cold Spring Harbor, New York, NY (1988).

Helenius et al., "Solubilization of membranes by detergents," *Biochim Biophys Acta* Mar. 25, 1975; 415(1):29-79. Review.

Hjelmeland, "Solubilization of native membrane proteins," *Methods Enzymol*. 1990;182:253-264.

Humphrey et al., "Experimental Infection of Hamsters with *Campylobacter jejuni*," *J. Infect. Dis*., Mar. 1985;151(3):485-493.

Karlyshev et al., "An improved physical and genetic map of *Campylobacter jejuni* NCTC 11168 (UA580)," *Microbiology*, Feb. 1998;144:503-508.

Keler et al., "Metachromatic Assay for the Quantitative Determination of Bacterial Endotoxins," *Anal. Biochem.*, Jul. 1986;156(1):189-193.

Morooka et al., "Motility as an Intestinal Colonization Factor for *Campylobacter jejuni*," *J. Gen. Microbiol.*, Aug. 1985;131(Pt 8):1973-1980.

Neilands, "Microbial envelope proteins related to iron," *Ann. Rev. Microbiol*., 36:285-309 (1982).

Newell et al., "Investigations on the role of flagella in the colonization of infant mice with *Campylobacter jejuni* and attachment of *Campylobacter jejuni* to human epithelial cell lines," *J. Hyg. Camb*. (London), Oct. 1985;95(2):217-227.

Nikaido et al., "Chapter 3: Outer Membrane," *Escherichia coli and Salmonella typhimurium: Cellular and Molecular Biology*, Neidhardt et al., eds., American Society for Microbiology, Washington, D.C., pp. 7-22 (1987).

Osborn et al., "Proteins of the outer membrane of gram-negative bacteria," *Annu Rev Microbiol*. 1980;34:369-422.

Palyada et al., "Iron Acquisition and Regulation in *Campylobacter jejuni*," J. Bacteriol., Jul. 2004;186(14):4714-4729.

Peterson, "Clinical Aspects of *Campylobacter jejuni* Infections in Adults," *West J. Med.*, Aug. 1994;161(2):148-152.

Pickett et al., "Iron Acquisition and Hemolysin Production by *Campylobacter jejuni*," *Infect. Immun.*, Sep. 1992;60(9):3872-3877.

Rae, "Injection Site Reactions," [online] In: 43rd Annual Florida Beef Cattle Short Course Proceedings, May 1994, Gainesville, FL. University of Florida, Department of Animal Sciences, [retrieved on Oct. 21, 2004]. Retrieved from the Internet: <http://www.animal.ufl.edu/extension/beef/documents/short94/rae.htm>; 3 pgs.

Raphael et al., "FeoB is not required for ferrous iron uptake in *Campylobacter jejuni*," *Can. J. Microbiol.*, Nov. 2003;49(11):727-731.

Ruiz-Palacios et al., "Experimental *Campylobacter* Diarrhea in Chickens," *Infect. Immun.*, Oct. 1981;34(1):250-255.

Schwartz et al., "Iron-regulated Proteins in Outer Membranes of *Campylobacter jejuni* Diarrhoea Isolates and Immune Response to the Proteins in Patients," *Zentralbl Bakteriol.*, Jan. 1994;280(3):338-347.

Schwartz et al., "Invasive Ability of *C. jejuni/coli* Isolates from Children with Diarrhea and the Effect of Iron-regulated Proteins," *Zentralbl Bakteriol.*, Apr. 1996;283(4):485-491.

Stanfield et al., "*Campylobacter* Diarrhea in an adult mouse model," *Microb. Pathog.*, Sep. 1987;3(3):155-165.

Thomas, "Prevalence of Melioidosis in Animals in Northern Queensland," *Aust. Vet. J.*, 1981;57:146-148.

Vandamme et al., "Proposal for a New Family, *Campylobacteraceae*," *Int. J. Syst. Bacteriol.*, 1991;41(3):451-455.

van Vliet et al., "Iron-Responsive Gene Regulation in a *Campylobacter jejuni fur* Mutant," *J. Bacteriol.*, Oct. 1998;180(20):5291-5298.

van Vliet et al., "The Iron-responsive regulator Fur of *Campylobacter jejuni* is expressed from two separate promoters," *FEMS Microbiol. Lett.*, Jul. 15, 2000; 188(2):115-118.

van Vliet et al., "The iron-induced ferredoxin FdxA of *Campylobacter jejuni* is involved in aerotolerance," *FEMS Microbiol. Lett.*, Mar. 15, 2001;196(2):189-193.

van Vliet et al., "The role of iron in *Campylobacter* gene regulation, metabolism and oxidative stress defense," *FEMS Microbiol Rev.*, Jun. 2002; 26(2):173-186.

Watson et al., eds., "Endotoxins and Their Detection With the Limulus Amebocyte Lysate Test," Proceedings of an International Conference on Endotoxin Standards and Limulus Amebocyte Lysate Use With Parenteral Drugs, Held at the Woods Hole Oceanographic Institution, Woods Hole, MA, Sep. 1981, Alan R. Liss, Inc., 150 Fifth Avenue, New York, NY (1982), title page, publication page, and table of contents only (5 pages).

Wooldridge et al., "Iron-Responsive Genetic Regulation in *Campylobacter jejuni*: Cloning and Characterization of a *fur* Homolog," *J. Bacteriol.*, Sep. 1994;176(18):5852-5856.

Arnaud et al., "Iron-Responsive Gene Regulation in a *Campylobacter jejuni fur* Mutant" *Journal of Bacteriology*, Oct. 1998; 180(20):5291-5298.

Blaser et al., "*Campylobacter jejuni* Outer Membrane Proteins are Antigenic for Humans" *Infection and Immunity*, Mar. 1984; 43(3):986-993.

Palyada et al., "Iron Acquisition and Regulation in *Campylobacter jejuni*" *Journal of Bacteriology*, Jul. 2004; 186(14):4714-4729.

Bos et al., "Biogenesis of the gram-negative bacterial outer membrane" *Current Opinion in Microbiology*, 2004; 7:610-616.

"CDC National Antimicrobial Resistance Monitoring System:Enteric Bacteria", datasheet, [online]. Centers for Disease Control, Washington D.C., 2002. [Retrieved Apr. 13, 2005.] Retrieved from the internet: <URL: http://www.cdc.gov/narms/; 7 pgs.

Crichton, "Chapter 3. Microbial iron uptake and intracellular release" In: *Inorganic Biochemistry of Iron Metabolism*, Burgess, (ed)., 1991, Ellis Horwood Limited, Chichester, England, Title page and pp. 59-76.

Crosa, "The Relationship of Plasmid-Mediated Iron Transport and Bacterial Virulence," *Annu. Rev. Microbiol.*, 1984;38:69-89.

E-Toxate® (Technical Bulletin No. 210). SIGMA Chemical Company, St. Louis, MO, 1998. pp. 1-4.

Hjelmeland, "[19] Solubilization of Native Membrane Proteins," in *Methods Enzymol. vol. 182 Guide to Protein Purification*, Deutscher (ed)., 1990 Academic Press: San Diego, CA. Title page, publishers page, and pp. 253-264.

Holmes et al., "*Campylobacter jejuni* Gene Expression in Response to Iron Limitation and the Role of Fur" *Microbiology*, 2005; 151:243-257.

Hodgson et al., "Experimental *Campylobacter* infection and diarrhoea in immunodeficient mice," *J. Med. Microbiol.*, 1998, 47:799-809.

Pei et al., "Pathogenesis of *Campylobacter fetus* Infections: Role of surface array proteins in virulence in a mouse model," *J. Clin. Invest.*, Apr. 1990; 85:1036-1043.

U.S. Appl. No. 12/269,636, filed Nov. 12, 2008, Emery et al.

U.S. Appl. No. 12/101,802, filed Apr. 11, 2008, Emery et al.

U.S. Appl. No. 12/393,275, filed Feb. 26, 2009, Emery et al.

Faraldo-Gomez et al., "Acquisition of Siderophores in Gram-Negative Bacteria," *Molecular Cell Biology*, Feb. 2003;4:105-116.

Baillon, et al., "An Iron-Regulated Alkyl Hydroperoxide Reductase (AhpC) Confers Aerotolerance and Oxidative Stress Resistance to the Microaerophilic Pathogen *Campylobacter jejuni*", *Journal of Bacteriology*, Aug. 1999; 181(16):4798-4803.

\* cited by examiner

CAMPYLOBACTER POLYPEPTIDES AND METHODS OF USE

CONTINUING APPLICATION DATA

This application claims the benefit of U.S. Provisional Application Ser. No. 60/504,119, filed 19 Sep. 2003, which is incorporated by reference herein.

BACKGROUND

*Campylobacter* spp. is part of the normal intestinal flora of a wide range of domestic and wild animals with a particular niche for the avian host. *Campylobacter* spp. do appear to have a limited ability to be pathogenic in domestic and wild animals animals. In cattle *C. fetus* subsp. *jejuni* and *C. fetus* subsp. *intestinalis* have been isolated from intestines and experimentally transmitted to preruminant and ruminant calves which developed clinical signs of fever, diarrhea and sporadic dysentery (Dannenberg et al. Am. J. Pathol. 34: 1099 (1958) and Thomas, Aust. Vet. J. 57: 146-148 (1981)). A syndrome of profuse watery diarrhea with fever, anorexia and depression in yearling sheep has also been reported with *Campylobacter fetus* as the causative agent. *Campylobacter* spp. has also been reported to cause clinical manifestations of dysentery, intestinal adenomatosis and hemorrhagic enteritis in pigs and horses, and mastitis in commercial dairy herds.

In humans, *Campylobacter* is the most commonly reported bacterial cause of endemic diarrheal illness worldwide. In the United States it is becoming the most prevalent cause of foodborne infection and affects more than 2 million people annually. In England and Wales, over 50,000 *campylobacter* cases are reported annually with no signs of decline of incidence. It is estimated that for every case reported to laboratory surveillance, another seven cases occur unreported. *C. jejuni* and *C. coli* are the two most commonly isolated species responsible for human Campylobacteriosis with *C. jejuni* now being the most frequently isolatable species.

The incubation period following ingestion of *C. jejuni* has been shown to be approximately 24-72 hours. The inoculum size required to induce clinical symptoms has been shown to be as few as 800 organisms. The rate of illness increases with increasing numbers of the organism ingested. Commonly reported symptoms of human Campylobacteriosis include diarrhea, fever, and abdominal cramping. Less frequently, *Campylobacter*, particularly *C. jejuni*, can cause secondary sequelae following an acute infection, including, reactive arthritis, kidney failure, Guillian-Barre, Reiter syndrome and other extra-intestinal symptoms.

The transmission of *Campylobacter* spp. to human populations is primarily through environmental contamination and contaminated foods, including poultry and poultry products such as eggs. *Campylobacter* spp. can be isolated from 30-100% of the birds in many domestic and wild avian species at any given time. In children, contact with puppies and kittens with diarrhea has been shown to be an important additional risk factor. Some additional sources of infection have resulted from drinking raw milk derived from cows having clinical mastitis caused by *Campylobacter*. All milkborne outbreaks have been associated with raw or improperly pasteurized milk.

The virulence and pathogenesis of *Campylobacter* spp. involves both host and pathogen specific factors. Many pathogen-specific virulence determinants contribute to the pathogenesis of these bacteria. The bacterial virulence of these bacteria is the result of many different attributes, which often contribute to different steps in the complicated series of events recognized as an infection. Exposure first takes place primarily by the consumption of contaminated water, food or by direct person to person contact. Once ingested the stages of infection common to these bacteria include attachment, colonization, proliferation, tissue damage, invasion and dissemination.

The first host barrier that *Campylobacter* must typically overcome is the mucosal surface. A single epithelial cell layer separates the host from the lumen of the gastrointestinal tract. This barrier and a plethora of other host antimicrobial mechanisms deter commensal, opportunistic and pathogenic microorganisms from establishing infection. Adherence to mucosal surfaces is a prerequisite of this pathogen to establish infection. One of the more pronounced clinical manifestations of intestinal colonization is diarrhea. This clinical syndrome has been proposed to be produced by the synthesis and excretion of enterotoxins that cause a net secretion of fluid and electrolytes (diarrhea). Other specific virulence factors include flagella, which assist the bacterium to overcome the clearing movement of peristalsis and enable the organism to enter and cross the mucous layer covering the epithelium (Black et al., J. Infect. Dis. 157:472-479 (1988), Caldwell et al., Infect Immun. 50:941-943 (1985), Morooka et al., J. Gen. Micro. 131:1973-1980 (1985) and Newell et al. J. Hyg. Camb. 95:217-227 (1985)). Other suspected determinants of pathogenicity include chemotaxis, iron-acquisition, host cell invasion, inflammation and active secretion and epithelial disruption with leakage of serosal fluid (Black et al. J. Infect. Dis. 157: 472-479 (1988)).

Divalent metal ions such as iron, cobalt, copper, magnesium, manganese, molybdenum, nickel, selenium, and zinc are trace elements often required for the survival of bacteria infecting both animal and human hosts. These trace metal elements are used by bacteria as cofactors for enzymes that catalyze biochemical reactions for various metabolic pathways and transport systems required by the organism. The metals iron, zinc and manganese are the three most important metals required for the survival of bacteria. Zinc ions are essential for RNA and DNA polymerase activity, whereas manganese is required for mitochondrial superoxide dismutase activity. Iron is the most extensively studied of all the metal ions with direct correlations on the virulence and pathogenesis of bacteria. Iron is essential for all life and is required for enzymatic and metabolic pathways of organisms at all phylogenic levels.

The ability of *Campylobacter* to evade the natural defense mechanisms of the vertebrate host depends in part on its ability to obtain host iron, which in turn directly influences the host-pathogen interaction. Because of iron's essential nature, vertebrate hosts have developed elaborate mechanisms to bind iron in body fluids (e.g., transferrin in blood and lymph fluids and lactoferrin in external secretions). These high affinity iron binding proteins create an iron restricted environment within the host reducing the level of iron to approximately $10^{-18}$ molar, a concentration too low to support the growth of nearly all bacteria. These iron sequestering mechanisms of the host act as a natural defense mechanism to combat bacterial invasion. To circumvent these iron-restrictive conditions many bacterial species have evolved mechanisms for obtaining iron. The most common mechanisms include the diffusion of soluble iron through porins and specialized transport systems that mediate the uptake of iron by siderophores. This latter system is by far the most widespread or ubiquitous mechanism for iron acquisition and involves the specific chelation of ferric iron by siderophores and the synthesis of their cognate transport systems, which permits the bacteria to continue to replicate and overcome the non-specific defense mechanisms of the host. Continued replication, and thus each step in the infectious process, is ultimately dependent on the ability of the organism to obtain iron from its host.

With so many basic functions relying on the availability of iron, bacteria have evolved a complex regulatory network for acquiring iron under varying physiological conditions. Iron is a divalent cation which exists both in the ferrous ($Fe^{2+}$) state and in the ferric ($Fe^{3+}$) state. Under anaerobic conditions, iron is present in the soluble ferrous form ($Fe^{2+}$) and can freely diffuse through outer membrane porins into the periplasm. For instance, in *E. coli* the FeoAB transport system present in the cytoplasmic membrane will transport the ferrous iron molecules into the cell cytoplasm. Under aerobic conditions and neutral pH, iron is primarily present in the insoluble ferric form ($Fe^{3+}$) and cannot pass through the outer membrane porins by passive diffusion. Instead, molecules called siderophores are secreted by bacteria, which have a high affinity for ferric iron. The ferric-siderophore complexes are recognized by receptors in the outer membrane, collectively referred to as the TonB-dependent receptors. These receptors, once bound to loaded siderophores, are believed to interact with TonB and its associated proteins localized in the periplasm and cytoplasmic membrane. These protein-protein interactions, though poorly understood, serve to provide the energy necessary to transport the ferri-siderophore complexes across the outer membrane and through the periplasmic space. ABC transport systems present in the cytoplasmic membrane serve to transport the iron-siderophore complexes across the cytoplasmic membrane. Reductase enzymes then serve to reduce ferric iron to its ferrous form, which dissociates it from the siderophore and releases iron into the cell.

Several species of pathogenic bacteria use additional mechanisms to obtain iron from mammalian hosts, including the direct binding of heme and hemoglobin. The receptor proteins that bind these iron-containing molecules most likely rely on the TonB complex for the energy required to transport heme across the outer membrane, similar to the iron-siderophore complexes. Specialized ABC transporters are then used to transport the heme across the cytoplasmic membrane. In addition, some bacteria secrete hemophores, small molecules that can bind heme and present it to receptors on the bacterial cell surface. Several pathogenic species also produce hemolysins, which are toxins that lyse red blood cells, releasing heme and hemoglobin for uptake by the bacteria.

The outer membrane proteins of gram-negative bacteria control the selective permeability of many essential nutrients critical to the survival of bacteria, including all pathogenic bacteria that cause disease in animals and man. This selective permeability of nutrients is controlled by a class of membrane proteins called porins. It now appears that the majority of the outer membrane proteins on the surface of gram-negative bacteria are porins, identified as the general porins (e.g., OmpF), monomeric porins (e.g., OmpA), the specific porins (e.g., the maltose-specific porin LamB) and the TonB-dependent, gated porins (e.g., the siderophore receptor FepA). The porin class of proteins generally share structural features, including the presence of beta-barrels that span the outer membrane.

Little is known regarding the iron-acquisition by *Campylobacter* spp. Studies indicate that *C. jejuni* does not synthesize siderophores (Field et al. Infect. Immun. 54: 126-132 (1986) and Pickett et al. Infect Immun. 60: 3872-3877 (1992)). This data has been confirmed by sequence analysis of *C. jejuni* genome in which no homologs of common siderophore synthesis genes were identified. *C. jejuni* is limited in the iron compounds it can use as demonstrated by various feeding assays. These assays have demonstrated that *C. jejuni* can use the siderophores enterochelin and ferrichrome but not aerobactin, desferal, ferritin, lactoferrin, or transferrin. Therefore, it has been suggested that other iron compounds are required to support the growth of *Campylobacter* spp. such as heme compounds like hemin and hemoglobin, ferric iron, and ferrous iron. The fact that *Campylobacter* has known transport systems for siderophores, yet is unable to synthesize them, suggests that these bacteria scavenge siderophores produced by other enteric pathogens (van Vliet et al. FEMS Microbiol. Rev. 26: 173-186 (2002)).

SUMMARY

The present invention provides an isolated metal regulated polypeptide obtainable from a *Campylobacter* spp., wherein the polypeptide is expressed by a *Campylobacter* spp. at a detectable level during growth under low metal conditions and is not expressed by the *Campylobacter* spp. at a detectable level during growth in high metal conditions, and a composition including the polypeptide. The isolated metal regulated polypeptide may have a molecular weight of between 150 kDa and 152 kDa, between 143 kDa and 145 kDa, between 123 kDa and 125 kDa, between 92 kDa and 94 kDa, between 88 kDa and 90 kDa, between 73 kDa and 75 kDa, between 69 kDa and 71 kDa, between 51 kDa and 53 kDa, between 50 kDa and 52 kDa, or between 38 kDa and 40 kDa. The composition may further include a second metal regulated polypeptide having a molecular weight of between 57 kDa and 59 kDa, between 54 kDa and 56 kDa, between 47 kDa and 49 kDa, between 42 kDa and 44 kDa, between 37 kDa and 39 kDa, or between 28 kDa and 30 kDa, wherein the second polypeptide is expressed by a *Campylobacter* spp. during growth in high metal conditions and expressed at an enhanced level during growth in low metal conditions.

The present invention also provides an isolated metal regulated polypeptide obtainable from a *Campylobacter* spp., wherein the polypeptide is expressed by a *Campylobacter* spp. during growth in high metal conditions and expressed at an enhanced level during growth in low metal conditions, and a composition including the polypeptide. The metal regulated polypeptide may have a molecular weight of between 57 kDa and 59 kDa, between 54 kDa and 56 kDa, between 47 kDa and 49 kDa, between 42 kDa and 44 kDa, between 37 kDa and 39 kDa, or between 28 kDa and 30 kDa.

The composition may further include a second metal regulated polypeptide having a molecular weight of between 150 kDa and 152 kDa, between 143 kDa and 145 kDa, between 123 kDa and 125 kDa, between 92 kDa and 94 kDa, between 88 kDa and 90 kDa, between 73 kDa and 75 kDa, between 69 kDa and 71 kDa, between 51 kDa and 53 kDa, between 50 kDa and 52 kDa, or between 38 kDa and 40 kDa, wherein the second polypeptide is expressed by a *Campylobacter* spp. at a detectable level during growth under low metal conditions and is not expressed by the *Campylobacter* spp. at a detectable level during growth in high metal conditions.

The present invention also includes methods for using the compositions disclosed herein, including methods for treating in infection in a subject, for treating a condition caused by a *Campylobacter* spp., for decreasing colonization of an animal. The methods include administering an effective amount of a composition to an animal, where the composition includes an isolated metal regulated polypeptide obtainable from a *Campylobacter* spp.

Also included in the present invention is a composition including an isolated whole cell preparation of a *Campylo-*

*bacter* spp., wherein the cells include either a metal regulated polypeptide expressed by the *Campylobacter* spp. during growth under low metal conditions and not expressed during growth in high metal conditions, a metal regulated polypeptide expressed by the *Campylobacter* spp. during growth in high metal conditions and expressed at an enhanced level during growth in low metal conditions, or the combination thereof.

DETAILED DESCRIPTION OF PREFERRED EMBODIMENTS OF THE INVENTION

Figure 1:
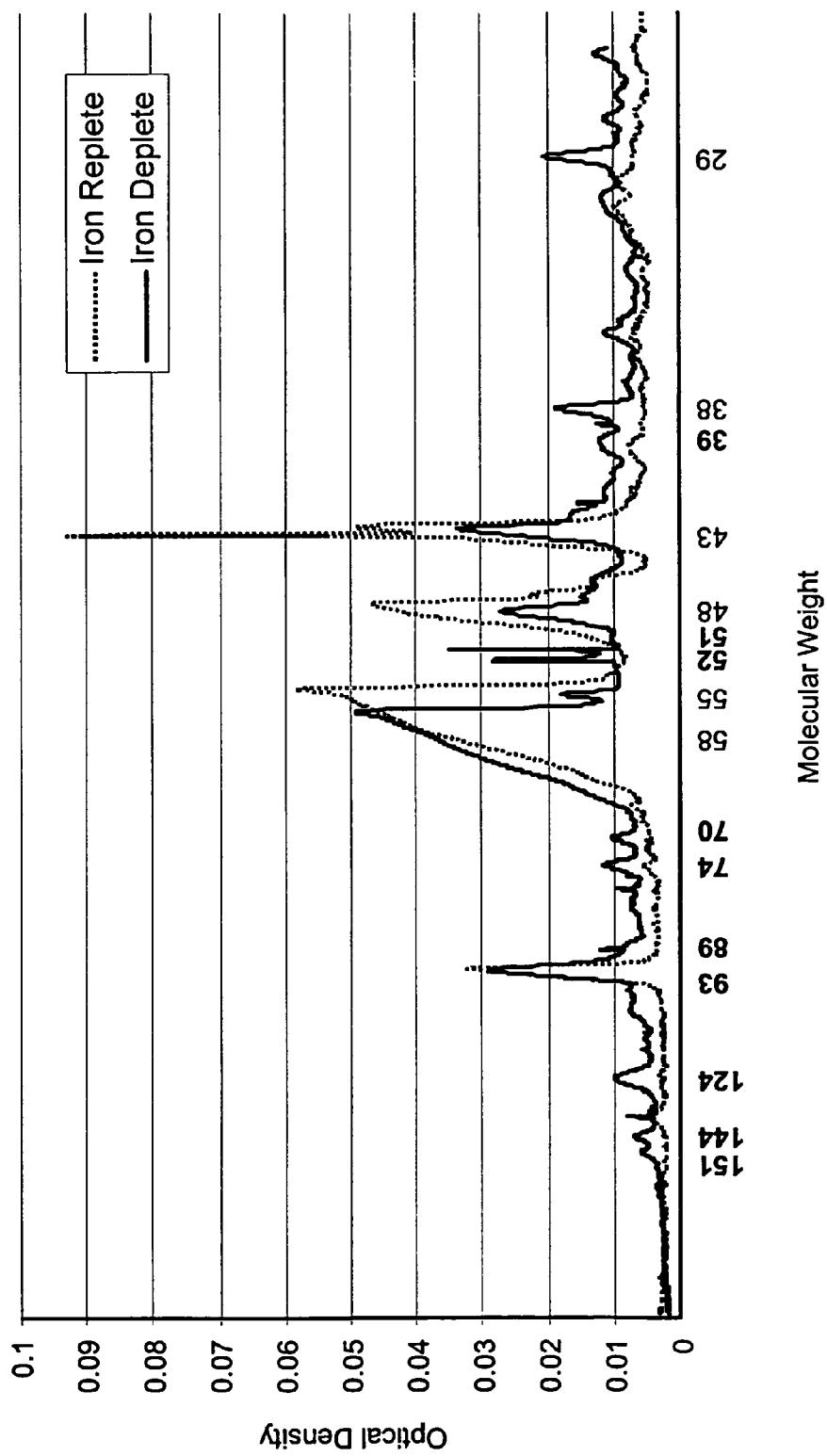
FIG. 1. Gel-image of *Campylobacter jejuni* extracted membrane protein profile expressed under iron-replete and iron-deplete growth conditions.

The present invention provides polypeptides and compositions including polypeptides. As used herein, "polypeptide" refers to a polymer of amino acids linked by peptide bonds. Thus, for example, the terms peptide, oligopeptide, protein, and enzyme are included within the definition of polypeptide. This term also includes post-expression modifications of the polypeptide, for example, glycosylations, acetylations, phosphorylations and the like. The term polypeptide does not connote a specific length of a polymer of amino acids. A polypeptide may be obtainable directly from a natural source, or can be prepared with the aid of recombinant, enzymatic, or chemical techniques. In the case of a polypeptide or polynucleotide that is naturally occurring, such polypeptide or polynucleotide is typically isolated. An "isolated" polypeptide is one that has been removed from its natural environment. For instance, an "isolated" polypeptide is a polypeptide that has been removed from the cytoplasm or from the outer membrane of a cell, and many of the polypeptides, nucleic acids, and other cellular material of its natural environment are no longer present. A "purified" polypeptide is one that is at least 60% free, preferably 75% free, and most preferably 90% free from other components with which they are naturally associated. Polypeptides that are produced outside the organism in which they naturally occur, e.g., through chemical or recombinant means, are considered to be isolated and purified by definition, since they were never present in a natural environment. Unless otherwise specified, "a," "an," "the," and "at least one" are used interchangeably and mean one or more than one.

The polypeptides of the present invention are obtainable from a member of the family Campylobacteriaceae, (Vandamme et al. Int. J. Syst. Bacteriol. 41: 451-455 (1991)), preferably the genus *Campylobacter*. A member of the genus *Campylobacter* is also referred to herein as *Campylobacter* spp. Examples of *Campylobacter* spp. from which polypeptides of the present invention may be obtained include *C. hyointestinalis, C. mucosalis, C. concisus, C. sputorum, C. jejuni, C. coli, C. lari, C. upsaliensis, C. rectus, C. curvus, C. hominis, C. fetus, C. intestinalis* and *C. doylei*. Preferably, the *Campylobacter* spp. from which polypeptides of the present invention may be obtained is *C. jejuni*. These microbes are commercially available from a depository such as American Type Culture Collection (ATCC). In addition, such microbes are readily obtainable by isolation techniques known and used in the art. For instance, a microbe may be derived from an infected animal as a field isolate, and used to obtain polypeptides of the present invention as described herein, or stored for future use, for example, in a frozen repository at about −20° C. to about −95° C., in an appropriate bacteriological media containing 20% glycerol, and other like media. Methods for obtaining the polypeptides from *Campylobacter* spp. are described herein.

A polypeptide of the present invention may be characterized by molecular weight. The molecular weight of a polypeptide, typically expressed in kilodaltons (kDa), can be determined using routine methods including, for instance, gel filtration, gel electrophoresis including sodium dodecyl sulfate (SDS) polyacrylamide gel electrophoresis, capillary electrophoresis, mass spectrometry, and liquid chromatography including HPLC.

In one aspect, the polypeptides of the present invention are metal regulated polypeptides. As used herein, a "metal regulated polypeptide" is a polypeptide that is expressed by a member of the genus *Campylobacter* at a greater level when the microbe is grown in low metal conditions compared to growth of same the microbe in high metal conditions. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron.

For instance, one type of metal regulated polypeptide produced by *Campylobacter* spp. is not expressed at detectable levels during growth of the microbe in high metal conditions but is expressed at detectable levels during growth in low metal conditions. Low metal conditions and high metal conditions are described in greater detail herein. Examples of such metal regulated polypeptides obtainable from a *Campylobacter* spp. have molecular weights (as determined by separation of the polypeptides using a stacking gel of about 4% on a resolving gel of about 10% under reducing and denaturing conditions of between 150 kDa and 152 kDa, between 143 kDa and 145 kDa, between 123 kDa and 125 kDa, between 92 kDa and 94 kDa, between 88 kDa and 90 kDa, between 73 kDa and 75 kDa, between 69 kDa and 71 kDa, between 50 kDa and 53 kDa, or between 38 kDa and 40 kDa. Preferably, the metal regulated polypeptides have molecular weights of 151 kDa, 144 kDa, 124 kDa, 93 kDa, 89 kDa, 74 kDa, 70 kDa, 52 kDa, 51 kDa, or 39 kDa.

Another type of metal regulated polypeptide produced by *Campylobacter* spp. is expressed at detectable levels during growth of the microbe in high metal conditions but expressed at higher levels during growth in low metal conditions. The expression of such polypeptides is referred to herein as "enhanced" during growth in low metal conditions. Examples of metal regulated polypeptides showing enhanced expression and obtainable from *Campylobacter* spp. have molecular weights (as determined by separation of the polypeptides using an about 10% SDS-PAGE gel under reducing and denaturing conditions) of between 57 kDa and 59 kDa, between 54 kDa and 56 kDa, between 47 kDa and 49 kDa, between 42 kDa and 44 kDa, between 37 kDa and 39 kDa, or between 28 kDa and 30 kDa. Preferably, the metal regulated polypeptides having enhanced expression have molecular weights of 58 kDa, 55 kDa, 48 kDa, 43 kDa, 38 kDa, or 29 kDa.

Whether a metal regulated polypeptide is expressed at a detectable level or has enhanced expression during growth in low metal conditions can be determined by methods useful for comparing the presence of polypeptides, including, for example, gel filtration, gel electrophoresis including sodium dodecyl sulfate (SDS) polyacrylamide gel electrophoresis, capillary electrophoresis, mass spectrometry, and liquid chromatography including HPLC. Separate cultures of a *Campylobacter* spp. are grown under high metal conditions and under low metal conditions, polypeptides of the present invention are isolated as described herein, and the polypeptides present in each culture are resolved and compared. Typically, an equal amount of polypeptide from each culture is used. For instance, when SDS polyacrylamide gel electrophoresis is used to compare the polypeptides, about 30 μg micrograms of polypeptide from each culture is used and loaded into a well. After running the gel and staining the polypeptides, the two lanes can be compared.

Preferably, polypeptides of the present invention have immunogenic activity. "Immunogenic activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody and/or a cellular immune response are produced.

Also provided by the present invention are whole cell preparations of a microbe, where the microbe expresses one or more of the polypeptides of the present invention. The cells present in a whole cell preparation are preferably inactivated such that the cells cannot replicate, but the immunogenicity of the polypeptides of the present invention expressed by the microbe is maintained. Typically, the cells are killed by exposure to agents such as glutaraldehyde, formalin, or formaldehyde.

Compositions

The present invention also provides compositions including at least about 1 of the polypeptides of the present invention, more preferably at least about 2, at least about 3, at least about 4, and so on, to about 8 polypeptides of the present invention. A composition can include polypeptides obtainable from 1 species of *Campylobacter*, or can be obtainable from a combination of 2 or more species of *Campylobacter*, for instance, *C. jejuni* and a second *Campylobacter* other than *C. jejuni*. Furthermore, a composition can include polypeptides obtainable from 2 or more strains of the same species of *Campylobacter*. For instance, a composition can include polypeptides obtainable from 2 different isolates of *C. jejuni*.

Optionally, a polypeptide of the present invention can be covalently bound to a carrier polypeptide to improve the immunological properties of the polypeptide. Useful carrier polypeptides are known to the art. The chemical coupling of a polypeptide of the present invention can be carried out using known and routine methods. For instance, various homobifunctional and/or heterobifunctional cross-linker reagents such as bis(sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl)cycloheane-1-carboxylate, sulfosuccinimidyl 4-(p-maleimido-phenyl) butyrate and (1-ethyl-3-(dimethyl-aminopropyl) carbodiimide can be used (Harlow and Lane, Antibodies, A Laboratory Manual, generally and Chapter 5, Cold Spring Harbor Laboratory, Cold Spring Harbor, New York, N.Y. (1988)).

Preferably, such compositions of the present invention include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (O-specific chain, the outer and inner core) and the lipid A region. The lipid A component of LPS is the most biologically active component of the LPS structure and together induce a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scaring or blemishes of the tissue at the injection site (see, for instance, Rae, Injection Site Reactions, available at www.animal.ufl.edu/short94/rae.htm).

The concentration of LPS can be determined using routine methods known to the art. Such methods typically include measurement of dye binding by LPS (see, for instance, Keler and Nowotny, *Analyt. Biochem.*, 156, 189-193 (1986)) or the use of a *Limulus amebocyte* lysate (LAL) test (see, for instance, Endotoxins and Their Detection With the *Limulus Amebocyte* Lysate Test, Watson et al., (eds.), Alan R. Liss, Inc., 150 Fifth Avenue, New York, N.Y. (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOXATE (Sigma Chemical Co., St. Louis, Mo.; see Sigma Technical Bulletin No. 210), and PYROTELL (Associates of Cape Cod, Inc., East Falmouth, Mass.). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for about 1 hour undisturbed at about 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, Md., Catalog No. 235503), and Associates of Cape Cod, Inc., (Catalog No. E0005). In general, when a composition of the present invention is prepared by isolating polypeptides from a microbe by a method as described herein (e.g., a method that includes disrupting and solubilizing the cells, and collecting the insoluble polypeptides), the amount of LPS in a composition of the present invention is less than the amount of LPS present in a mixture of the same amount of the microbe that has been disrupted under the same conditions but not solubilized. Typically, the level of LPS in a composition of the present invention is decreased by, in increasing order of preference, at least about 50%, at least about 60%, at least about 70%, at least about 80%, or at least about 90% relative to the level of LPS in a composition prepared by disrupting, but not solubilizing, the same microbe.

The present invention also provides compositions including a whole cell preparation of at least 1, at least 2, at least 3, at least 4, at least 5, or 6 *Campylobacter* spp.

The compositions of the present invention optionally further include a pharmaceutically acceptable carrier. "Pharmaceutically acceptable" refers to a diluent, carrier, excipient, salt, etc, that is compatible with the other ingredients of the composition, and not deleterious to the recipient thereof. Typically, the composition includes a pharmaceutically acceptable carrier when the composition is used as described herein. The compositions of the present invention may be formulated in pharmaceutical preparations in a variety of forms adapted to the chosen route of administration, including routes suitable for stimulating an immune response to an antigen. Thus, a composition of the present invention can be administered via known routes including, for example, oral; parental including intradermal, subcutaneous, intramuscular, intravenous, intraperitoneal, etc., and topically, such as, intranasal, intrapulmonary, intramammary, intravaginal, intrauterine, intradermal, and rectally etc. It is foreseen that a composition can be administered to a mucosal surface, such as by administration to the nasal or respiratory mucosa (e.g. spray or aerosol), to stimulate mucosal immunity, such as production of secretory IgA antibodies, throughout the animal's body.

A composition of the present invention can also be administered via a sustained or delayed release implant. Implants suitable for use according to the invention are known and include, for example, those disclosed in Emery and Straub (WO 01/37810 (2001)), and Emery et al. (WO 96/01620 (1996)). Implants can be produced at sizes small enough to be administered by aerosol or spray. Implants also include nanospheres and microspheres.

A composition of the present invention is administered in an amount sufficient to treat certain conditions as described herein. The amount of polypeptides or whole cells present in a composition of the present invention can vary. For instance, the dosage of polypeptides can be between 0.01 micrograms (μg) and 300 mg, typically between 0.1 mg and 10 mg. When the composition is a whole cell preparation, the cells can be present at a concentration of, for instance, $10^6$ bacteria/ml, $10^7$ bacteria/ml, $10^8$ bacteria/ml, or $10^9$ bacteria/ml. For an injectable composition (e.g. subcutaneous, intramuscular, etc.) the polypeptides may be present in the composition in an amount such that the total volume of the composition administered is 0.5 ml to 5.0 ml, typically 1.0-2.0 ml. When the composition is a whole cell preparation, the cells are preferably present in the composition in an amount that the total volume of the composition administered is 0.5 ml to 5.0 ml, typically 1.0-2.0 ml. The amount administered will vary depending on various factors including, but not limited to, the specific polypeptides chosen, the weight, physical condition and age of the animal, and the route of administration. Thus, the absolute weight of the polypeptide included in a given unit dosage form can vary widely, and depends upon factors such as the species, age, weight and physical condition of the animal, as well as the method of administration. Such factors can be determined by one of skill in the art. Other examples of dosages suitable for the invention are disclosed in Emery et al. (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., a polypeptide or whole cell of the present invention) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldiocradecylammonium bromide (DDA), pyridine, aluminum hydroxide, oils, saponins, alpha-tocopherol, polysaccharides, emulsified paraffins (including, for instance, those available from under the tradename EMULSIGEN from MVP Laboratories, Ralston, Nebr.), ISA-70, RIBI and other substances known in the art.

In another embodiment, a composition of the invention including a pharmaceutically acceptable carrier can include a biological response modifier, such as, for example, IL-2, IL-4 and/or IL-6, TNF, IFN-alpha, IFN-gamma, and other cytokines that effect immune cells. An immunizing composition can also include other components known to the art such as an antibiotic, a preservative, an anti-oxidant, or a chelating agent.

Methods of Making

Polypeptides and whole cell preparations of the present invention may be obtained by incubating a member of the genus *Campylobacter* under conditions that promote expression of one or more of the polypeptides described herein. The present invention also includes compositions prepared by the processes disclosed herein. Typically, such conditions are low metal conditions. As used herein, the phrase "low metal conditions" refers to an environment, typically bacteriological media, that contains amounts of a free metal that cause a microbe to express metal regulated polypeptides. As used herein, the phrase "high metal conditions" refers to an environment that contains amounts of a free metal that cause a microbe to either not express one or more of the metal regulated polypeptides described herein, or to decrease expression of such a polypeptide. Low metal conditions are generally the result of the addition of a metal chelating compound to a bacteriological medium. High metal conditions are generally present when a chelator is not present in the medium, and/or a metal is added to the medium. Examples of metal chelators include natural and synthetic compounds. Examples of natural compounds include plant phenolic compounds, such as flavenoids. Examples of flavenoids include the copper chelators catechin and naringenin, and the iron chelators myricetin and quercetin. Examples of synthetic copper chelators include, for instance, tetrathiomolybdate, and examples of synthetic zinc chelators include, for instance, N,N,N',N'-Tetrakis(2-pyridylmethyl)-ethylene diamine. Examples of synthetic iron chelators include 2,2'-dipyridyl (also referred to in the art as α,α'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. Preferably, 2,2'- dipyridyl is used for the chelation of iron. Typically, 2,2'-dipyridyl is added to the media at a concentration of at least 0.0025 micrograms/milliliter (µg/ml), at least 0.025 µg/ml, or at least 0.25 µg/ml. High levels of 2,2'-dipyridyl can be 10 µg/ml, 20 µg/ml, or 30 µg/ml.

It is expected that a *Campylobacter* spp. with a mutation in a fur gene will result in the constitutive expression of many, if not all, of the metal regulated polypeptides of the present invention. A fur gene has been identified in a *C. jejuni* (van VLiet et al., J. Bacteriol., 180, 5291-5298, (1998)). The production of a fur mutation in a *Campylobacter* spp. can be produced using routine methods including, for instance, electroporation and genetic constructs useful for gene knock-out in gram negative bacteria.

Many *Campylobacter* spp. are able to grow in low metal conditions in vitro in artificial media only after adaptation. For instance, a *Campylobacter* spp. can be adapted to low iron conditions in vitro by growth in the presence of low concentrations of an iron chelator and, after growth in a medium containing the chelator, gradually increasing the concentration of the chelator. For instance, a *Campylobacter* spp. can be adapted to growth in low iron conditions by adding 10 µg/ml of 2,2'-dipyridyl to a medium, and gradually increasing the concentration of the chelator to a greater concentration, for instance, 20 µg/ml.

The medium used to incubate the microbe and the volume of media used to incubate the microbe can vary. When a *Campylobacter* spp. microbe is being evaluated for the ability to produce the polypeptides described herein, the microbe can be grown in a suitable volume, for instance, 10 milliliters to 1 liter of medium. When a microbe is being grown to obtain polypeptides for use in, for instance, administration to animals, the microbe may be grown in a fermentor to allow the isolation of larger amounts of polypeptides. Methods for growing microbes in a fermentor are routine and known to the art. The conditions used for growing a microbe preferably include a metal chelator, more preferably an iron chelator, for instance 2,2'-dipyridyl, a pH of between about 6.5 and about 7.5, preferably between about 6.9 and 7.1, and a temperature of about 37° C. When a fermentor is used, the culture may be purged with an appropriate gas, for instance, carbon dioxide, to maintain microaerophilic conditions. Members of the genus *Campylobacter* are microaerophilic organism, thus growth conditions do not include levels of oxygen that will prevent growth.

In some aspects of the invention, a *Campylobacter* spp. may be harvested after growth. Harvesting includes concentrating the microbe into a smaller volume and suspending in a media different than the growth media. Methods for concentrating a microbe are routine and known to the art, and include, for example, filtration and/or centrifugation. Typically, the concentrated microbe is suspended in decreasing amounts of buffer. Preferably, the final buffer includes a metal chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, 8.5, and/or including one or more proteinase inhibitors (e.g., phenylmethanesulfonyl fluoride). Optionally and preferably, the concentrated microbe is frozen at −20° C. or below until disrupted.

When the *Campylobacter* spp. is to be used as a whole cell preparation, the harvested cells may be processed using routine and know methods to inactivate the cells. Alternatively, when a *Campylobacter* spp. is to be used to prepare polypeptides of the present invention, the *Campylobacter* spp. may be disrupted using chemical, physical, or mechanical methods routine and known to the art, including, for example, french press, sonication, or homoginization. Preferably, homoginization is used. As used herein, "disruption" refers to the breaking up of the cell. Disruption of a microbe can be measured by methods that are routine and known to the art, including, for instance, changes in optical density. Typically, a microbe is subjected to disruption until the percent transmittance is increased by 20% when a 1:100 dilution is measured. The temperature during disruption is typically kept low, preferably at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., polypeptides, nucleic acids, carbohydrates) into the aqueous phase of the buffer in which the microbe was disrupted, and the formation of aggregates of insoluble cellular materials. The conditions for solubilization preferably result in the aggregation of polypeptides of the present invention into insoluble aggregates that are large enough to allow easy isolation by, for instance, centrifugation.

Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known to the art, including, for instance, changes in optical density. Typically, the solubilization is allowed to occur for at least 24 hours, more preferably, at least 48 hours, most preferably, at least 60 hours. The temperature during disruption is typically kept low, preferably at 4° C.

The insoluble aggregates that include the polypeptides of the present invention may be isolated by methods that are routine and known to the art. Preferably, the insoluble aggregates are isolated by centrifugation. Typically, centrifugation of outer membrane polypeptides that are insoluble in detergents requires centrifugal forces of at least 50,000×g, typically 100,000×g. The use of such centrifugal forces requires the use of ultracentrifuges, and scale-up to process large volumes of sample is often difficult and not economical with these types of centrifuges. The methods described herein provide for the production of insoluble aggregates large enough to allow the use of significantly lower centrifugal forces (for instance, 46,000×g). Methods for processing large volumes at these lower centrifugal forces are available and known to the art. Thus, the insoluble aggregates can be isolated at a significantly lower cost.

Optionally and preferably, the sarcosine is removed from the isolated polypeptides. Methods for removing sarcosine from the isolated polypeptides are known to the art, and include, for instance, diafiltration, precipitation, hydrophobic chromatography, ion-exchange chromatography, and/or affinity chromatography, and ultra filtration and washing the polypeptides in alcohol by diafiltration. After isolation, the polypeptides suspended in buffer and stored at low temperature, for instance, −20° C. or below.

Polypeptides of the present invention may also be isolated from *Campylobacter* spp. using methods that are known to the art. The isolation of the polypeptides may be accomplished as described in, for instance, Emery et al., (U.S. Pat. No. 5,830,479) and Emery et al., (U.S. Patent Application U.S. 20030036639 A1).

In those aspects of the present invention where a whole cell preparation is to be made, after growth of a *Campylobacter* spp. the microbe can be killed with the addition of an agent such as glutaraldehyde, formalin, or formaldehyde, at a concentration sufficient to inactivate the cells in the culture. For instance, formalin can be added at a concentration of about 3% (vol:vol). After a period of time sufficient to inactivate the cells, the cells can be harvested by, for instance, diafiltration and/or centrifugation, and washed.

Methods of Use

An aspect of the present invention is further directed to methods of using the compositions of the present invention. The methods include administering to an animal an effective amount of a composition of the present invention. Preferably, the composition further includes a pharmaceutically acceptable carrier. The composition can be administered at a time that maternal antibody may be present, for instance, as early as one day of age, or at a later time during the life of the animal. The animal can be, for instance, an ungulate, a bird, a human, or a companion animal. Examples of birds include commercial poultry such as turkeys, chickens, ducks, pheasant, and ostrich. Examples of ungulates include animals that are bovine (including, for instance, cattle), caprine (including, for instance, goats), ovine (including, for instance, sheep), porcine (including, for instance, swine), equine (including, for instance, horses), members of the family Cervidae (including, for instance, deer, elk, moose, caribou and reindeer), and Bison (including, for instance, buffalo). Examples of companion animals include dogs and cats.

In some aspects, the methods may further include additional administrations (e.g., one or more booster administrations) of the composition to the animal to enhance or stimulate a secondary immune response. A booster can be administered at a time after the first administration, for instance, 1 to 8 weeks, preferably 2 to 4 weeks, after the first administration of the composition. Subsequent boosters can be administered one, two, three, four, or more times annually. Without intending to be limited by theory, it is expected that annual boosters will not be necessary, as an animal will be challenged in the field by exposure to members of the genus *Campylobacter* expressing polypeptides having epitopes that are identical to or structurally related to epitopes present on the polypeptides present in the composition administered to the animal.

In one aspect, the invention is directed to methods for inducing the production of antibody in an animal or by recombinant techniques. The antibody produced includes antibody that specifically binds at least one polypeptide present in the composition. In this aspect of the invention, an "effective amount" is an amount effective to result in the production of antibody in the animal. Methods for determining whether an animal has produced antibodies that specifically bind polypeptides present in a composition of the present invention can be determined as described herein.

The method may be used to produce antibody that specifically binds polypeptides expressed by a microbe other than the microbe from which the polypeptides of the composition were isolated. As used herein, an antibody that can "specifically bind" a polypeptide is an antibody that interacts with the epitope of the antigen that induced the synthesis of the antibody, or interacts with a structurally related epitope. At least some of the polypeptides present in the compositions of the present invention typically include epitopes that are conserved in the polypeptides of different species and different genera of microbes. Accordingly, antibody produced using a composition derived from one microbe is expected to bind to polypeptides expressed by other microbes and provide broad spectrum protection against gram negative organisms. Examples of gram negative microbes to which the antibody specifically binds are enteropathogens, for instance, members of the family Enterobacteriaceae.

In one aspect the invention is also directed to treating an infection in an animal caused by a member of the genus *Campylobacter*. The method includes administering an effective amount of the composition of the present invention to an animal having an infection caused by a member of the genus *Campylobacter*, and determining whether the *Campylobacter* spp. causing the infection has decreased. Methods for determining whether an infection is caused by a member of the genus *Campylobacter* are routine and known to the art.

In another aspect, the present invention is directed to methods for treating one or more symptoms of certain conditions in animals, preferably humans, that may be caused by, or associated with, infection by a member of the genus *Campylobacter*. Examples of conditions caused by *Campylobacter* spp. infections include diarrhea, fever, and abdominal cramping, as well as symptoms such as bacteremia, septic arthritis, Guilain-Barre syndrome Reiter syndrome (Peterson, Wes. J. Med. 161: 148-152 (1994) and Allos, J. Infest Dis. 176: S125-128 (1997)). Treatment of these conditions can be prophylactic or, alternatively, can be initiated after the development of a condition described herein. Treatment that is prophylactic, for instance, initiated before a subject manifests symptoms of a condition caused by *Campylobacter* spp., is referred to herein as treatment of a subject that is "at risk" of developing the condition. Typically, an animal "at risk" of developing a condition is an animal likely to be exposed to a *Campylobacter* spp. causing the condition. For instance, the animal is present in an area where the condition has been diagnosed in at least one other animal, or is being transported to an area where a *Campylobacter* spp. is endemic, and/or where conditions caused by *Campylobacter* spp. are prevalent. Accordingly, administration of a composition can be performed before, during, or after the occurrence of the conditions described herein. Treatment initiated after the development of a condition may result in decreasing the severity of the symptoms of one of the conditions, or completely removing the symptoms. In this aspect of the invention, an "effective amount" is an amount effective to prevent the manifestation of symptoms of a condition, decrease the severity of the symptoms of a condition, and/or completely remove the symptoms. The potency of a composition of the present invention can be tested according to routine methods (see, for instance, Stanfield et al., Microb Pathog., 3:155-165 (1987), Fox et al., Am. J. Vet. Res., 48:85-90 (1987), Ruiz-Palacios et al., Infect. Immun., 34:250-255 (1981), and Humphrey et al., J. Infect. Dis., 151:485-493 (1985)). Methods for determining whether an animal has the conditions disclosed herein and symptoms associated with the conditions are routine and known to the art.

The present invention is also directed to decreasing colonization of the intestinal tract or reproductive tract of an animal by a *Campylobacter* spp. The method includes administering an effective amount of a composition of the present invention to an animal colonized by, or at risk of being colonized by a gram negative microbe, preferably, a *Campylobacter* spp. In this aspect of the invention, an "effective amount" is an amount effective to decrease colonization of the animal by the microbe. Colonization of an animal's intestinal tract by a microbe can be determined by measuring the presence of the microbe in the animal's feces. Methods for evaluating the colonization of an animal's reproductive tract by a microbe are routine and known to the art. It is expected that decreasing the colonization of an animal by a *Campylobacter* spp. will reduce transmission of the *Campylobacter* spp. to humans.

A composition of the invention can be used to provide for passive immunization against infection by *Campylobacter* spp. For instance, the composition can be administered to an animal to induce the production of immune products, such as antibodies, which can be collected from the producing animal and administered to another animal to provide passive immunity. Immune components, such as antibodies, can be collected to prepare antibody compositions from serum, plasma, blood, colostrum, etc. for passive immunization therapies. Antibody compositions including monoclonal antibodies, anti-idiotypes, and/or recombinant antibodies can also be prepared using known methods. Passive antibody compositions and fragments thereof, e.g., scFv, Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods and spray dried or lyophilized for later use in a concentrated or reconstituted form. Passive immunizing preparations may be particularly advantageous for treatment of acute systemic illness, or passive immunization of young animals that failed to receive adequate levels of passive immunity through maternal colostrum.

Another aspect of the present invention provides methods for detecting antibody that specifically binds polypeptides of the present invention. These methods are useful in, for instance, detecting whether an animal has antibody that specifically binds polypeptides of the present invention, and diagnosing whether an animal may have an infection caused by *Campylobacter* spp. Preferably, such diagnostic systems are in kit form. The methods include contacting an antibody with a preparation that includes at least one polypeptide of the present invention to result in a mixture. Preferably, the antibody is present in a biological sample, more preferably blood, serum, milk, mucosal secretions, or colostrum. The method further includes incubating the mixture under conditions to allow the antibody to specifically bind a polypeptide to form a polypeptide:antibody complex. As used herein, the term "polypeptide:antibody complex" refers to the complex that results when an antibody specifically binds to a polypeptide. The preparation that includes the polypeptides present in a composition of the present invention may also include reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase. The methods for detecting the presence of antibodies that specifically bind to polypeptides of the present invention can be used in various formats that have been used to detect antibody, including radioimmunoassay and enzyme-linked immunosorbent assay.

The present invention also provides a kit for detecting antibody that specifically binds polypeptides of the present invention. The kit includes at least one polypeptide of the present invention in a suitable packaging material in an amount sufficient for at least one assay. Optionally, other reagents such as buffers and solutions needed to practice the invention are also included. Instructions for use of the packaged polypeptides are also typically included.

As used herein, the phrase "packaging material" refers to one or more physical structures used to house the contents of the kit. The packaging material is constructed by known methods, preferably to provide a sterile, contaminant-free environment. The packaging material has a label which indicates that the polypeptides can be used for detecting antibodies induced by infection with *Campylobacter* spp. In addition, the packaging material contains instructions indicating how the materials within the kit are employed to detect such antibodies. As used herein, the term "package" refers to a solid matrix or material such as glass, plastic, paper, foil, and the like, capable of holding within fixed limits the polypeptides. Thus, for example, a package can be a microtiter plate well to which microgram quantities of polypeptides have been affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLE

Example 1

Production and Isolation of Metal Regulated Proteins

*Campylobacter* spp. *jejuni* can be grown under controlled fermentation conditions so as to express proteins, including proteins associated with the outer membrane. The bacteria can be harvested and the proteins can then be isolated and used as immunogens in a composition described in detail in the following example. Microaerophilic conditions for growth of *C. jejuni* on plates and in small liquid cultures were established by incubation in an anaerobic jar containing a CAMPYPAK (BBL, Sparks, Md.) gas generator system. A master seed stock of a *Campylobacter jejuni* originating from a turkey was prepared by inoculating the isolate into 200 ml of Porcine Brain Heart Infusion Broth (P-BHI, Difco) containing 0.025% metabisulfite (Sigma) and containing 10 to 20 micrograms per milliliter (µg/ml) of 2,2-dipyridyl (Sigma-Aldrich St. Louis, Mo.). The culture was grown without stirring at 16 hours at 37° C. under microaerophilic conditions. Prior to growth in a starter culture, the *C. jejuni* was adapted to grow in the iron chelator 2,2-dipyridyl by repeatedly subculturing the isolate into increasing concentrations of the iron chelator, beginning at 10 µg/ml, and increasing to 20 µg/ml. The bacterium was collected by centrifugation at 10,000×g. The bacterial pellet was resuspended into 20 ml P-BHI containing 20% glycerol, and sterilely dispensed into 2 ml cryogenic vials (1 ml per vial) and stored at −90° C. The isolate was given the identification Campy-1, and established as a master seed. The master seed was expanded into a working seed that was then used for the production of metal regulated proteins. This strain was deposited with the American Type Culture Collection, P.O. Box 1549, Manassas, Va., 20108, USA, on Sep. 17, 2004, and granted accession number PTA-6215. The deposit was made under the Budapest Treaty on the International Recognition of the Deposit of Microorganisms for the Purposes of Patent Procedure.

Example 2

Production of Metal Regulated Proteins

Fermentation: A cryogenic vial of the working seed (1 ml at 10$^9$ CFU/ml) was used to inoculate 130 ml of 37° C. P-BHI or T-Soy containing 15-20 micrograms (μg) 2,2-dipyridyl and 0.025% metabisulfite (Sigma) and incubated in an anaerobic jar containing a CAMPYPAK (BBL, Sparks, Md.) gas generator system. The culture was incubated at 37° C. for 12-24 hours at which point was sterilely transferred into 1.3 liters of the above media. This second culture was allowed to grow for an additional 10 hours at 37° C. This culture was used to inoculate a 20-liter BIOFLO IV bench-top fermentor, (New Brunswick Scientific Co, Edison N.J.) charged with 13 liters of the above-described media. The pH was held constant between 6.9 and 7.1 by automatic titration with 30% NaOH and 10% HCL. The stirring speed was adjusted to 100 revolutions per minute (rev/minute), and the culture was maintained under microaerophilic conditions. The culture was allowed to grow continuously at these conditions for 24 hours at which point the fermentation was terminated by lowering the temperature of the fermentor to 10° C.

Harvest: The bacterial fermentation was concentrated and washed using a Millipore PELLICON Tangential Flow Filter assembly (Millipore Corporation, Bedford, Mass.), equipped with a 25 ft$^2$ screen-channel series Alpha 300K CENTRASETTE filter (Pall Filtron). The original culture volume of 13 liters was reduced to 2.5 liters. The bacterial retentate was then adjusted to 25 liters using physiological saline (0.85%) and then concentrated again to 2.5 liters to help remove any contaminates not associated with the cells, e.g., secreted proteins. The retentate (2.5 liters) was adjusted to 15 liters using sterile Osmotic Shock Buffer (OMS) containing 7.26 grams/liter Tris-base and 0.93 grams/liter EDTA adjusted to a pH of 8.5. The retentate was mixed thoroughly and equally dispensed (3.0 liters each) into 5 sterile four liter NALGENE containers and placed into a −20° C. freezer for storage. The pellet mass was calculated by centrifuging 30 ml samples of the fermented culture and final harvest. Briefly, pre-weighted 50 ml NALGENE conical tubes were centrifuged at 39,000×g for 90 minutes in a BECKMAN J2-21 centrifuge using a JA-21 rotor (Beckman Instruments, Palo Alto Calif.). At the end of the run, the supernatant was poured off and the tubes were weighed again. The pellet mass was calculated for each stage.

Disruption (Homogenization): Three liters of frozen bacterial cell slurry in OMS was thawed at 4° C. (180 g pellet mass). The liquid culture suspension was aseptically transferred into a 50 liter jacketed process tank containing 44 liters OMS pH 8.5 containing 0.1 grams thimerosal/liter as preservative. The bulk bacterial suspension was chilled to 4° C. with continuous mixing for 18 hours at 200 rpm at which time was disrupted by homogenization. Briefly, the 50 liter tank containing the bacterial suspension was connected to a model 12.51H Rannie Homogenizer, (APV Systems, Rosemont, Ill.). A second 50 liter jacketed process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of each pass, fluid was circulated at 70 psi through the homogenizer and back to the tank of origin, while the homogenizer pressure was adjusted to 13,500 psi. Prior to the first pass, two pre-homogenizing samples were withdrawn from the homogenizer to establish a baseline for determining the degree of disruption and monitoring of pH. The degree of disruption was monitored by transmittance (% T at 540 nm at 1:100 dilution) compared to the non-homogenized sample. The bacterial suspension was passed three times through the homogenizer to give a final percent transmittance between 78-83% T at a 1:100 dilution.

After homogenization, Sodium Lauroyl Sarcosinate (HAMPOSYL L-30, Chem/Serv, Minneapolis, Minn.) was aseptically added to the homogenized bacterial suspension for solubilization. The amount of Sarcosine (30%) added equaled 0.0664 times the solubilizing volume, in liters, (1.0 gram sarcosine/4.5 grams pellet mass). The process tank was removed from the homogenizer and kept at 4° C. while stirring at 240 rpm for 60-70 hours.

Protein harvest: The proteins within the solubilized process fluid was collected by centrifugation using T-1 SHARPLES, (Alfa Laval Seperations, Warminster, Pa.). Briefly, the solubilized homogenate was fed into six SHARPLES with a feed rate of 250 ml/minute at 17 psi at a centrifugal force of 60,000×g. The temperature during centrifugation was kept at 4° C. The solubilized homogenate was passed 2 times across the centrifuges. The protein was collected, resuspended and dispensed in 10 liters Tris-buffer pH 8.5 containing 0.3% formalin (Sigma) as preservative.

Diafiltration: The protein suspension (10 liters) was adjusted to 60 liters using sterile Tris-buffer, pH 8.5. The suspension was washed and dialyzed using a Millipore PELLICON Tangential Flow Filter assembly (Millipore Corporation), equipped with a 25 ft$^2$ screen-channel series Alpha 10K CENTRASETTE filter (Pall Filtron) to remove residual sarcosine. The protein solution was concentrated by filtration to a target volume of 10 liters at which point 50 liters of Tris-buffer pH 7.4 containing 5% isopropyl alcohol was slowly added to the concentrate from a second process tank. Isopropyl alcohol is thought to cause a slight unfolding of the protein structure allowing for the removal of bound sarcosine without compromising the immunogenicity of the proteins. Diafiltration continued until the pH stabilized to 7.4 at which point 50 liters Tris-buffer pH 7.4 was slowly added by diafiltration to remove residual alcohol. The protein suspension was then concentrated to approximately 5 liters. The protein concentrate was equally dispensed (500 ml) into ten sterile 1 liter NALGENE containers and stored at −20° C. until use.

Example 3

Analysis of Proteins

The protein profile of the *C. jejuni* isolate grown in iron-replete and/or iron-deplete media was examined by SDS-PAGE. Briefly, the organism was grown from a frozen master seed stock by sub-culturing into 25 ml of P-BHI containing 0.025% metabisulfite and 15 to 20 micrograms per milliliter (μg/ml) of 2,2-dipyridyl (Sigma-Aldrich St. Louis, Mo.) and/or P-BHI with metabisulfite containing 200 uM ferric chloride incubated for 18 hours at 37° C. while stirring at 100 rpm. At 18 hours of incubation, 5 ml of each culture was transferred into 500 ml of pre-incubated (37° C.) iron-deplete and/or iron-replete media. Cultures were allowed to grow for 18 hours at 37° C. while stirring at 100 rpm. At 18 hours post incubation each culture was centrifuged at 10,000×g for 20 minutes. The bacterial pellet was resuspended in a 100 ml of tris-buffered saline and centrifuged at 10,000×g for 10 minutes to remove any contaminating media proteins. The bacterial pellet from the iron-replete and iron-deplete media was resuspended in 40 ml of Tris-buffered saline pH 7.2 and disrupted by sonicaton. The disrupted bacterial suspension was clarified by centrifugation at 32,000×g for 12 minutes. The supernatant was collected and solubilized by the addition of sodium lauroyl sarcosinate 4% vol/vol at 4° C. for 24 hours. The detergent-insoluble OMP-enriched fraction was collected by centrifugation at 32,000×g for 2.5 hours at 4° C. The OMP pellet was resuspended in 200 μl tris-buffer at pH 7.2 and stored at −90° C. A sample of each extract was resolved on a 10% SDS-PAGE gel to compare the protein profile obtained from cells grown in iron-replete and iron-deplete media. The gel was scanned using a BioRad GS-800 densitometer to compare the difference in the protein profile of *C. jejuni* grown under iron-replete and iron-deplete conditions.

Example 4

Preparation of the Immunizing Compositions Derived from *C. jejuni*

The composition made from *C. jejuni* as described in example 2 was used to prepare a vaccine. A stock vaccine was prepared from the composition by diluting the antigen into phosphate buffered saline (PBS) containing 8.0 g/l NaCl, 0.2 g/l KCl, 1.44 g/l $Na_2HPO_4$ and 0.24 g/l $KH_2PO_4$ pH 7.4 containing 10% aluminum hydroxide (REHYDRAGEL, Reheis Chemical Company Berkeley Heights, N.J.). The aluminum hydroxide suspension (500 µg total protein/ml) was then emulsified into the commercial adjuvant, EMULSIGEN, (MVP Laboratories, Ralston, Nebraska) using a IKA ULTRA-TURRAX T-50 homogenizing vessel (IKA, Cincinnati, Ohio). A mouse dose was administered to give a final dose of 50 µg total protein in a 0.1 ml injectable volume with an adjuvant concentration of 22.5% vol/vol. A placebo was prepared by replacing the antigen with physiological saline in the above formulation and emulsifying the suspension into EMULSIGEN to give an adjuvant concentration of 22.5%.

Example 5

Preparation of Challenge Organism

The *C. jejuni* isolate as described above was used for challenge. Briefly, the isolate from a frozen stock (example 1) was streaked onto a blood agar plate and incubated at 37° C. for 18 hours. Several colonies were sub-cultured into 50 ml P-BHI containing 15 µg/ml 2,2' dipyridyl and 0.025% metabisulfite. The culture was incubated at 37° C. for 16 hours, and then centrifuged at 10,000×g for 10 minutes at 4° C. to pellet the bacteria. The bacterial pellet was washed once by centrifugation (10,000×g for 15 minutes) at 4° C. The final pellet was resuspended in 25 ml of P-BHI without dipyridyl. Just prior to challenge, 1 ml of the above bacterial suspension was serially diluted ten fold to enumerate the number of CFU/dose.

Example 6

Mouse Vaccination and Oral Challenge Study with *Camplylobacter jejuni* (Evaluation of Fecal Shedding)

In this experiment the efficacy of the *C. jejuni* vaccine was carried out against a live oral challenge in mice. The outcome parameters used to evaluate vaccine efficacy in this experiment were 1) individual mouse mortality, and 2) differences in the concentration of *Campylobacter* being shed between treatment groups after challenge. Twenty (N=20) female CF-1 mice obtained from Harlan Breeding Laboratories (Indianapolis, Ind.) weighing 16-22 grams were equally distributed into two groups (10 mice/group). Mice were housed in polycarbonate mouse cages (Ancore Corporation, Bellmore, N.Y.). Two cages were used, one for each treatment group. Groups were designated as placebo, non-vaccinated (Group 1) and vaccinated (Group 2). Food and water were supplied ad libitum to all mice.

Mice were vaccinated three times at 14 day intervals subcutaneously with the placebo and/or the *C. jejuni* vaccines described in Example 4. The volume of vaccine administered was 0.1 ml/mouse. Fourteen days after the third vaccination, mice in groups 1 and 2 were orally challenged with *C. jejuni* at $4.05 \times 10^9$ colony forming units (CFU) in a volume of 0.2 cc. The challenge organism was prepared as described in example 5.

To enumerate the difference in fecal shedding between the control and vaccinated groups, mouse droppings were collected at 12 hours post challenge. Droppings were collected by placing a sterile pad on the floor of each cage 1 hour prior to collection. At each time period the pad was removed and placed into a laminar flow hood. Using a sterilely flamed forceps, twenty individual droppings were randomly collected. The forceps were flamed between each collection so as not to cross-contaminate samples. Individual droppings were placed into sterile saline dilution blanks (0.9 ml), two droppings per tube, to give ten tubes. Each sample was macerated using a sterile 1 ml pipette and serially diluted 10 fold. Dilutions were plated on *Campylobacter* Agar (Difco Laboratories, Detroit, Mich.) incubated at 37 $C_5$% $CO_2$ for 72 hours. The number of bacteria was enumerated for each sample and the $\log_{10}$ colony forming units were averaged for each treatment group at each time period.

Figure 2:
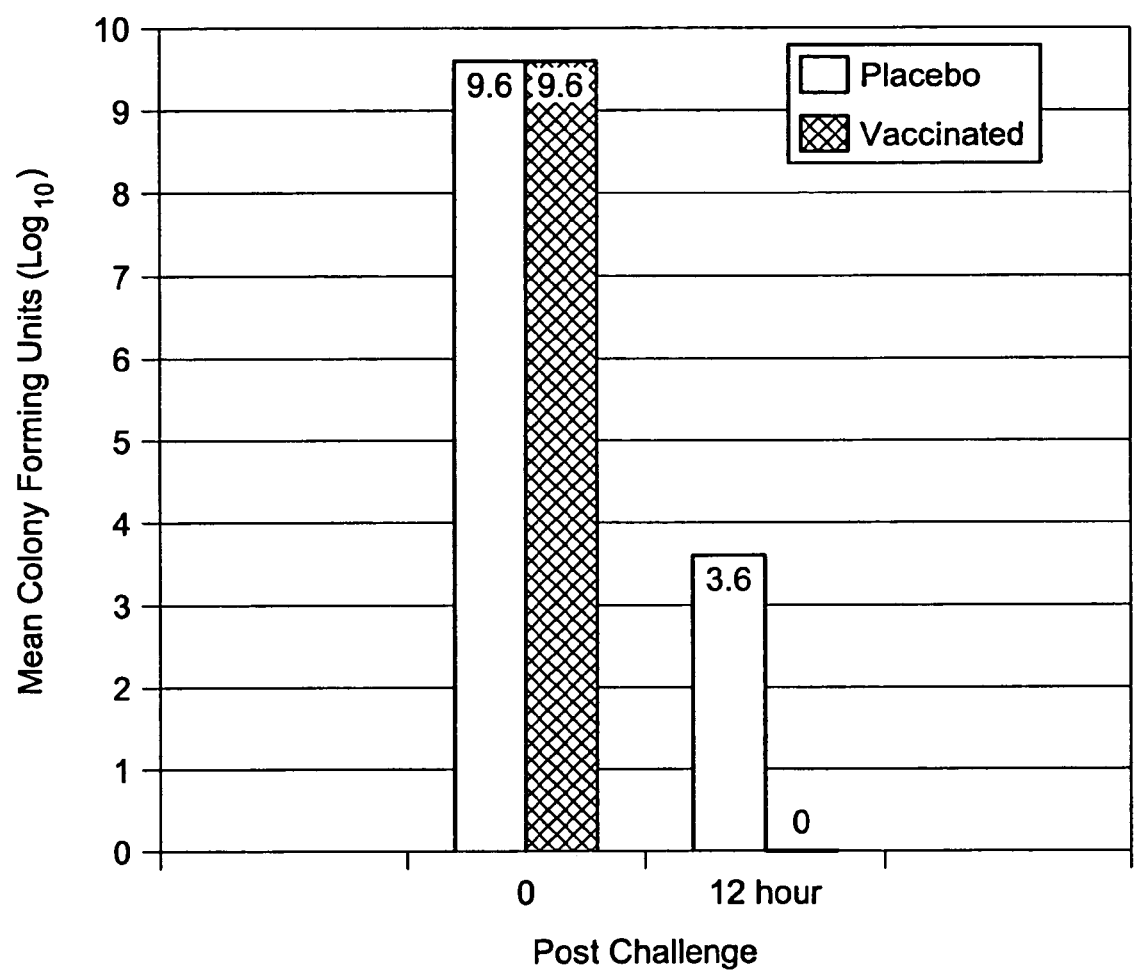
FIG. 2. The difference in fecal shedding between vaccinated and non-vaccinated mice after oral challenge with *Campylobacter jejuni*. Log 10 CFU, mean number of bacteria in fecal sample.

Table 1 shows the difference in the fecal shedding between vaccinated and non-vaccinated mice after an oral challenge with *C. jejuni* at each time period. There was a large difference between treatment groups in the amount of *Campylobacter* shedding in feces post-challenge. The challenge dose represented as time 0 in Table 1 shows the initial inoculum given to each mouse. Within twelve hours post challenge there was a dramatic decrease in the amount of *Campylobacter* being shed from the vaccinated group as compared to the Placebo group. Averaged across the study period and accounting for repeated estimates, vaccinates shed less *Campylobacter* at each sampling period when compared to non-vaccinates, with a degree of significance of P=0.005. The amount of *Campylobacter* being shed in the vaccinated group dramatically declined with each sampling period as compared to the non-vaccinated Placebo group (FIG. 2). At 12 hours post challenge the difference in the amount of *Campylobacter* being shed between the vaccinated and non-vaccinated group was greater then 3 logs (Table 1, FIG. 2).

TABLE 1

The Difference in Shedding of *Campylobacter jejuni* Between the Non-Vaccinated and Vaccinated Treatment Groups after Oral Challenge.

| | Mean $\log_{10}$ Colony Forming Units | |
|---|---|---|
| Sampling Times | Group 1 (Non-vaccinated) | Group 2 (Vaccinated) |
| Challenge Dose (time 0) | 9.607 | 9.607 |
| 12 hours | 3.6 | 0(a) |

(a)Detection limit of the test was $10^{-1}$

The experiment was terminated at 12 hours due to a contamination with a *Pseudomonas aeruginosa* which grew through the selective antibiotics in the *Campylobacter* agar at all subsequent samplings. No mortality was observed in any mice after challenge. The results clearly demonstrate that subcutaneous vaccination with the composition results in a significant difference (P=0.005) in the colonization of *Campylobacter* compared to a non-vaccinated Placebo group.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of administering to an animal colonized by or at risk of being colonized by *Campylobacter jejuni*, an amount of a composition comprising isolated iron-regulated polypeptides obtainable from *Campylobacter jejuni* when incubated in a culture medium comprising an iron chelator and not obtainable when grown in the culture medium without the iron chelator, wherein the amount is an amount effective to decrease colonization of the intestinal tract of the animal by *Campylobacter jejuni*, and wherein the isolated iron-regulated polypeptides have molecular weights of between 150 kDa and 152 kDa, between 143 kDa and 145 kDa, between 123 kDa and 125 kDa, between 88 kDa and 90 kDa, between 73 kDa and 75 kDa, between 69 kDa and 71 kDa, between 51 kDa and 53 kDa, between 50 kDa and 52 kDa, and between 38 kDa and 40 kDa as determined by 10% SDS-PAGE.

2. A method of reducing fecal shedding of *Campylobacter jejuni* in an animal colonized by *Campylobacter jejuni* comprising administering to the animal an amount of a composition comprising isolated iron-regulated polypeptides obtainable from the *Campylobacter jejuni* when incubated in a culture medium comprising an iron chelator and not obtainable when grown in the culture medium without the iron chelator, wherein the amount is an amount effective to reduce the fecal shedding and wherein the isolated iron-regulated polypeptides have molecular weights of between 150 kDa and 152 kDa, between 143 kDa and 145 kDa, between 123 kDa and 125 kDa, between 88 kDa and 90 kDa, between 73 kDa and 75 kDa, between 69 kDa and 71 kDa, between 51 kDa and 53 kDa, between 50 kDa and 52 kDa, and between 38 kDa and 40 kDa as determined by 10% SDS-PAGE.

3. The method of claim 1, wherein the animal is a mammal or a bird.

4. The method of claim 2, wherein the animal is a mammal or a bird.

5. The method of claim 1, wherein the *Campylobacter jejuni* is *C. jejuni* ATCC strain PTA-6215.

6. The method of claim 2, wherein the *Campylobacter jejuni* is *C. jejuni* ATCC strain PTA-6215.

* * * * *